United States Patent [19]

Herzberg

[11] Patent Number: 5,171,223
[45] Date of Patent: * Dec. 15, 1992

[54] DRAINAGE AND INSTRUMENT DUCT FOR THE ARTHROSCOPY

[75] Inventor: Wolfgang Herzberg, Wedel/Holstein, Fed. Rep. of Germany

[73] Assignee: Renate Dunsch-Herzberg und Gudrun Voss, Hamburg, Fed. Rep. of Germany

[*] Notice: The portion of the term of this patent subsequent to Oct. 1, 2008 has been disclaimed.

[21] Appl. No.: 648,573

[22] Filed: Jan. 31, 1991

Related U.S. Application Data

[62] Division of Ser. No. 505,020, Apr. 5, 1990, Pat. No. 5,053,009.

[51] Int. Cl.5 .................................. A61M 29/00
[52] U.S. Cl. ........................................ 604/104
[58] Field of Search .......................... 604/104-109, 604/256, 280, 281, 247, 264

[56] References Cited

U.S. PATENT DOCUMENTS

| | | | |
|---|---|---|---|
| 1,863,057 | 6/1932 | Innes | 604/105 |
| 2,072,346 | 3/1937 | Smith | 604/105 X |
| 3,713,447 | 1/1973 | Adair | 604/105 |
| 4,571,241 | 2/1986 | Christopher | 604/104 |
| 5,053,009 | 10/1991 | Herzberg | 604/104 |

Primary Examiner—John D. Yasko
Attorney, Agent, or Firm—Anderson Kill Olick & Oshinsky

[57] ABSTRACT

Figure 1:
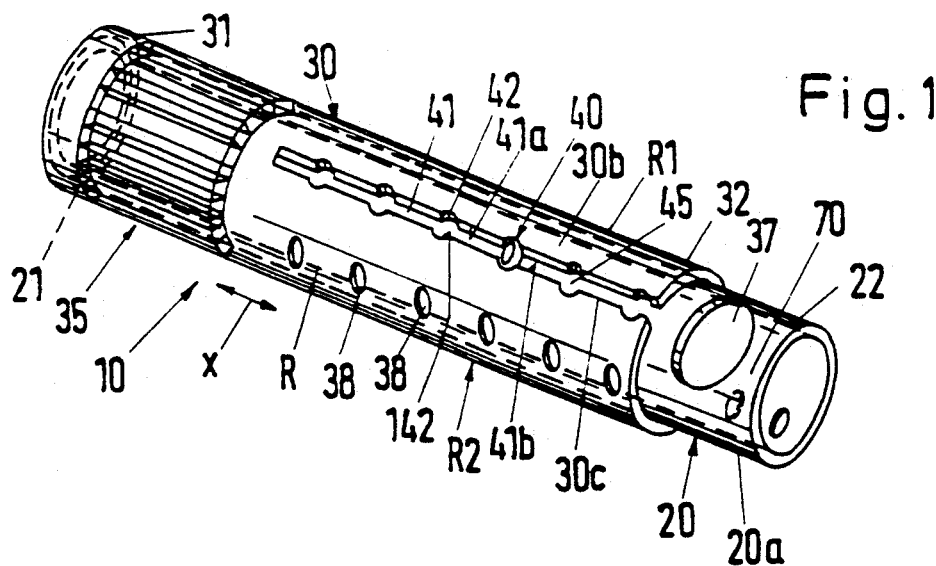

The luxation-proof drainage and instrument duct for the arthroscopy comprises a hollow cylinder (20) and a sleeve (30) longitudinally displaceable thereupon which are interconnected at the one end, while the sleeve (30), within the area of its connecting end, is constructed in such a way that, when the sleeve (30) is displaced towards the connection plane, a terminal area of the sleeve is outwardly expanded in a basket-like manner over the circumference of the sleeve, the basket-like expanded sleeve end being provided with a plurality of perforations (135') disposed so as to be distributed over the circumference and in side-by-side arrangement. The sleeve (30) is arrested on the hollow cylinder (20) in the expanded state of the terminal section of the sleeve (FIG. 1).

9 Claims, 8 Drawing Sheets

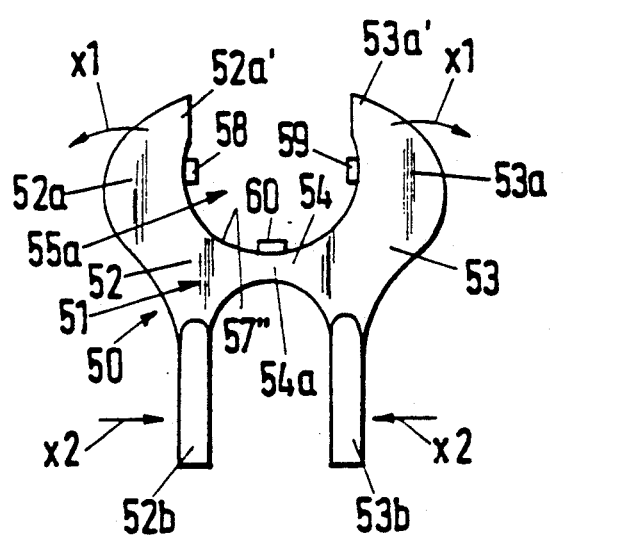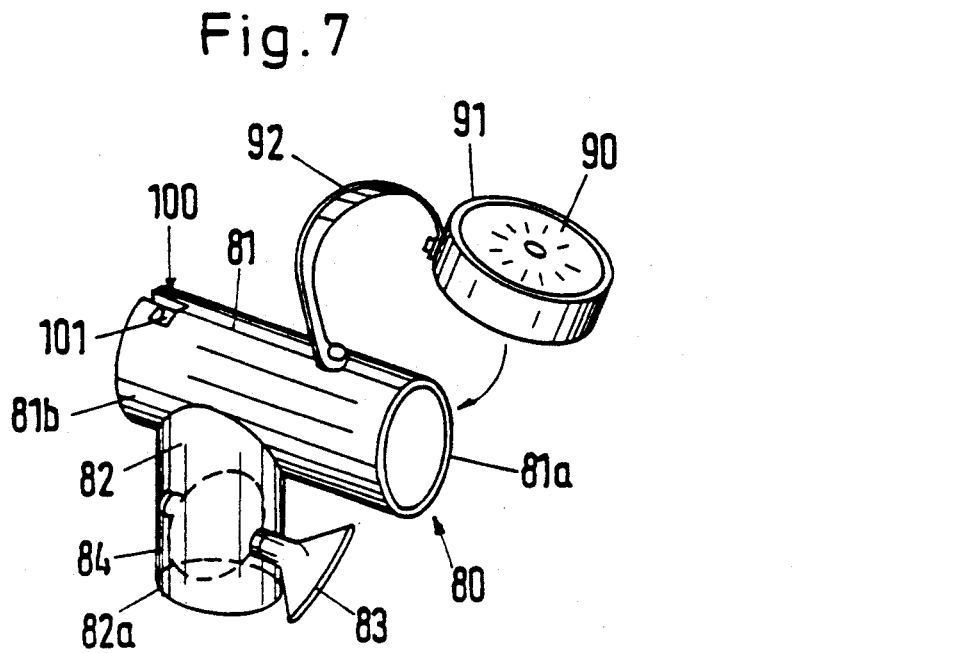

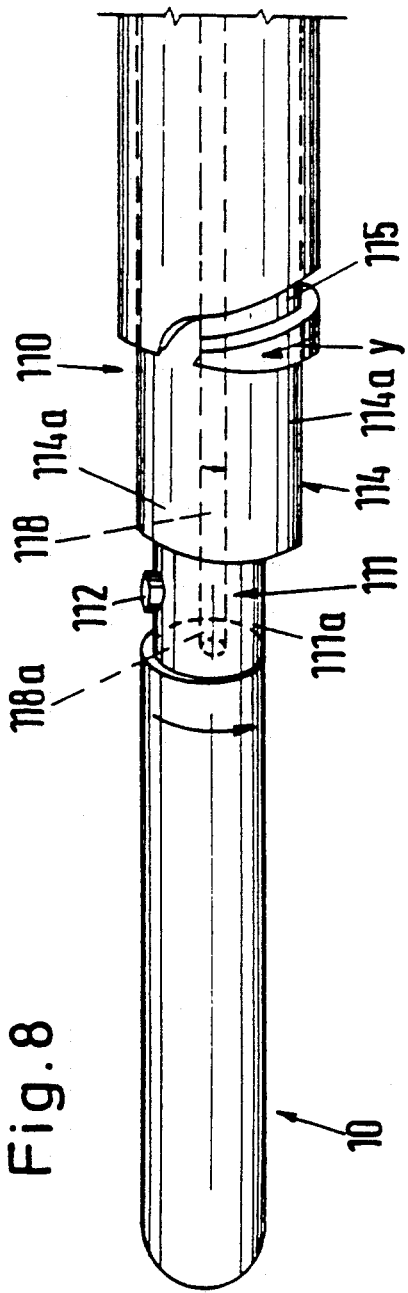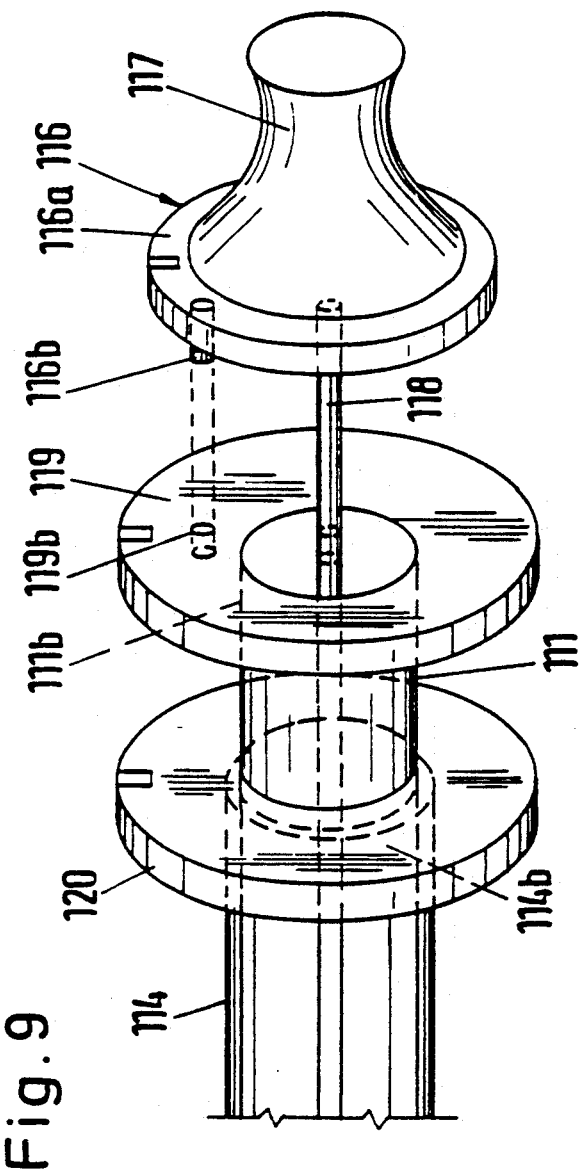
Fig. 8
Fig. 9

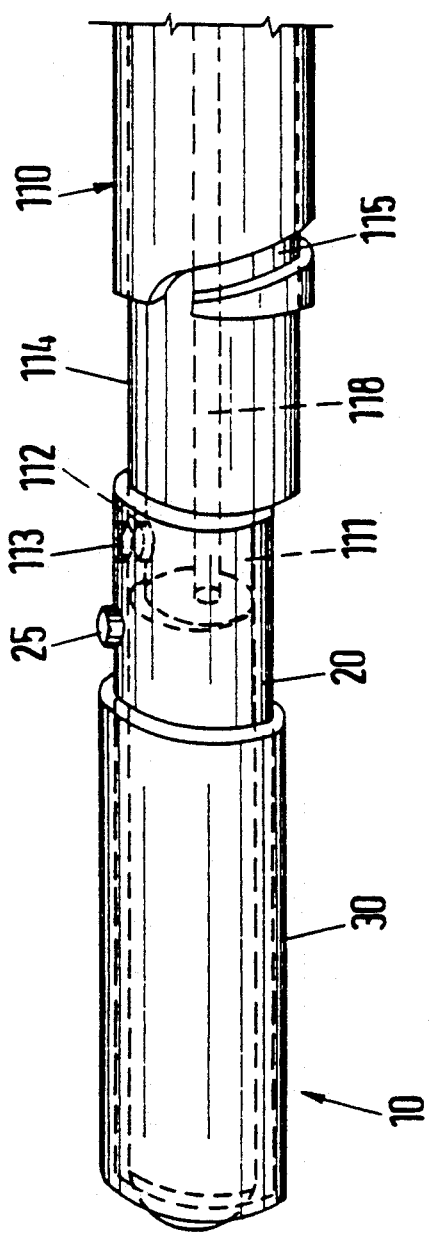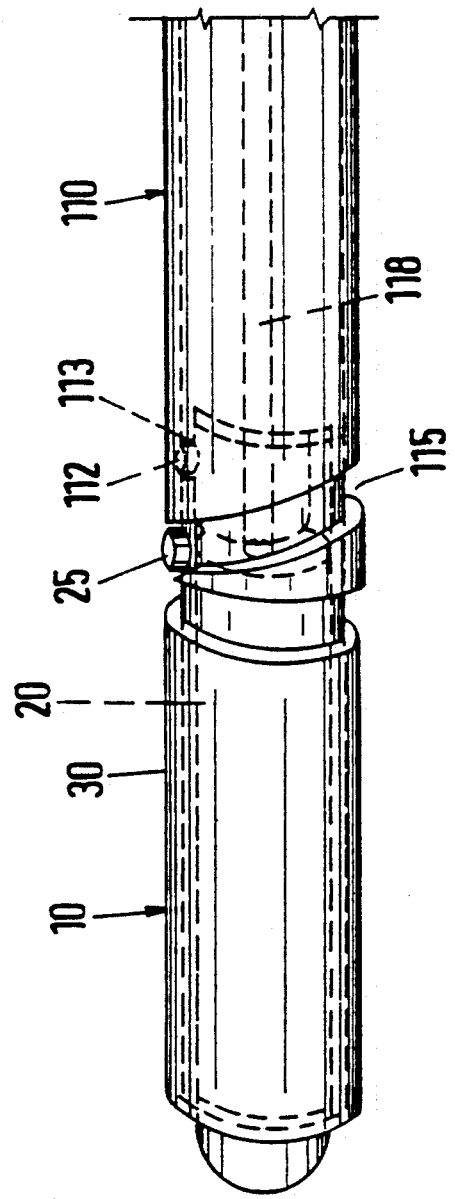

Fig. 12
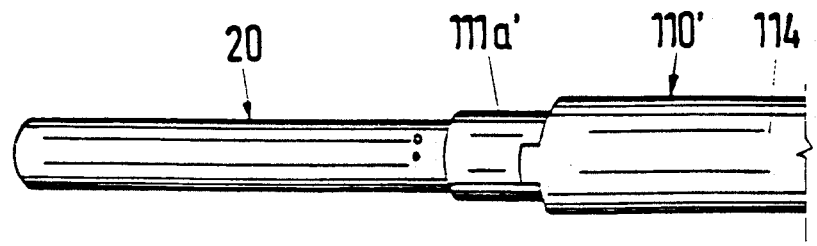
Fig. 13
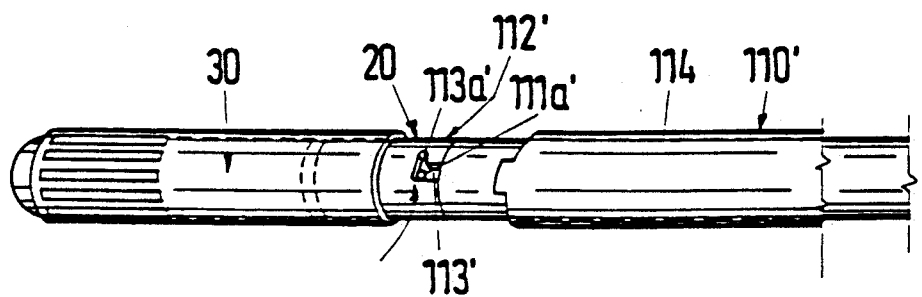
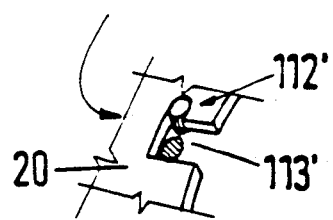
Fig. 14
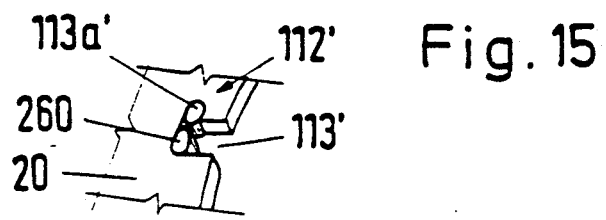
Fig. 15

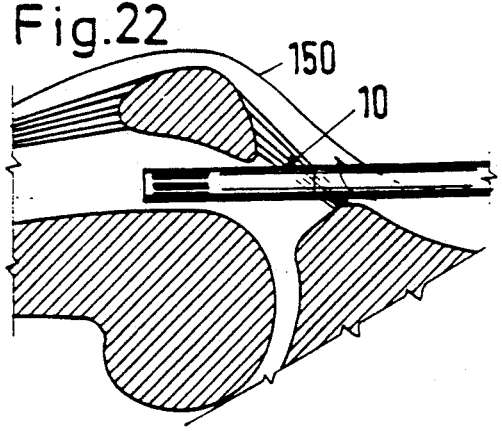
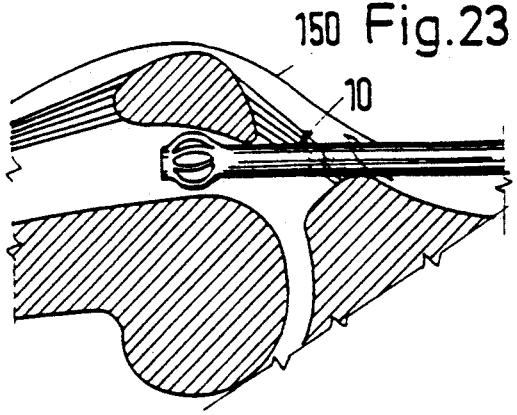
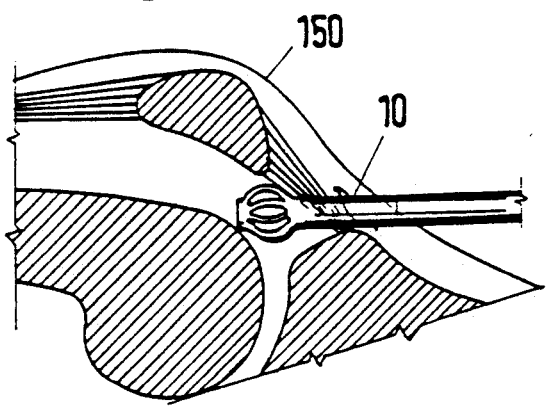
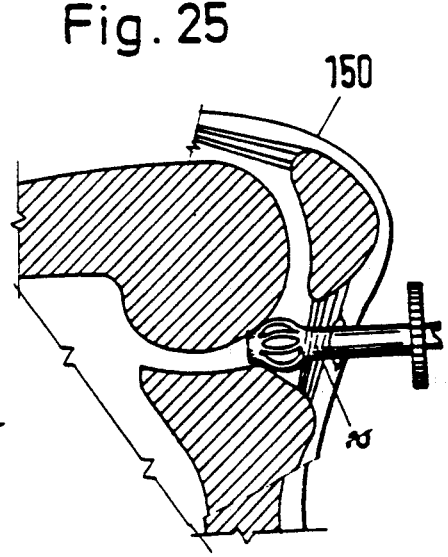
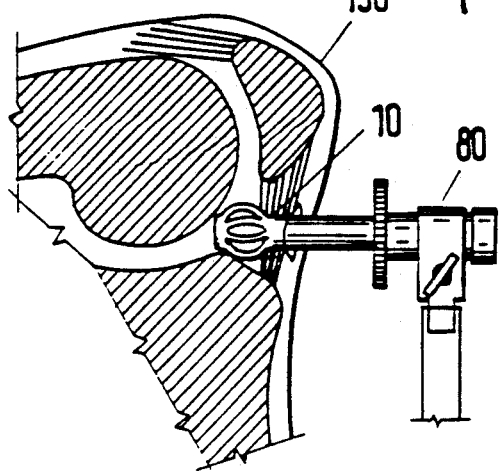

DRAINAGE AND INSTRUMENT DUCT FOR THE ARTHROSCOPY

This is a divisional application of Ser. No. 07/505,020, filed Apr. 5, 1990 now U.S. Pat. No. 5,053,009.

The present invention relates to a drainage and instrument duct for the arthroscopy.

The anthroscopic operation can only be performed in an aqueous medium. Conditions of clear visibility can only be maintained when a steady flow of liquid passes through the joint. If the supply of liquid can be ensured by simple means via the optics duct, then the unobstructed drainage from the joint is subject to problems:

If the drainage point is remote from the location of the operation —thus from the supply—then the flushing effect, due to the merely laminar flow conditions at the location of the operation, often is inadequate; in addition to this, freely suspended gristle nd meniscus particles are carried far into the joint;

If the point of drainage is brought into the vicinity of the location of the operation, then space-related problems frequently arise, for due to the confined conditions is is problematical to prevent the drainage duct from slipping out unnoticed from the joint interior and, with this, to become obstructed;

Freely suspended particles may be drawn by suction to the drainage aperture and obstruct the same since the normal internal diameters mostly are too small to allow the particles to pass;

The removal of particles from the joint—also of larger fragments —often causes difficulties; it can happen that a meniscus fragment seized by forceps is lost in the tissue layers when being extracted;

If the sole aim is to convey tissue fragments out of the joint, then their collection in order to subject the tissue to a histological examination often remains unconsidered—the fragments are merely flushed out together with the liquid.

Various obtuse inlet and outlet cannulae are known which are additionally provided with perforations and which, within the coupling area, are fitted with a stop cock. Said cannulas are in most cases too thin and too long so that, on eh one hand, they will not allow thicker fragments to pass, thicker forceps being likewise unable to pass on account of their length and they are also impassable to slightly angled instruments. Furthermore, thin endless hosepipes are known which are provided with lateral perforations and which ar drawn through the joint far from the location of the operation. Also known are the so-called ports which can serve as a guide duct for the optics and the instruments. The termination of the inserted instrument is produced with the aid of a rubber seal. Said ports are relatively long and possess no retaining mechanism which secures the position inside the joint.

The invention is based on the technical problem of providing a luxation-proof drainage and instrument duct for the athroscopy with as large as possible an internal diameter than can be advanced far into the joint and with which the ensuring of the recovery of smallest tissue particles is rendered possible for histological examinations or tests to be carried out later without that released, minute gristle/meniscus particles are carried into the joint during the flushing process. In addition, it is intended to prevent a soaking of the area surrounding the location of the operation through the flushing liquid, and a fixation of the drainage and instrument duct is to be rendered possible. This technical problem is solved by the features characterized in the claim 1.

Such a drainage and instrument duct constructed in accordance with the invention ensures the recovery of the minutest tissue particles for histological tests to be performed later. The duct prevents a saturation of the area surrounding the location of the operation by the flushing liquid. Released gristle/meniscus particles are not entrained into the joint during the flushing. Due to the arrestability of the drainage and instrument duct in its operative position, a slipping out of the duct from the interior is prevented. Moreover, a clogging of the drainage aperture by small particles is prevented.

The hollow cylinder of the drainage and instrument duct is dimensioned so as to be relatively short and has as large as possible an internal diameter and can be advanced far into the joint so as to ensure the secure position therein. Owing to the circumstance that the hollow cylinder, in connection with the sleeve supported on the same, renders possible a basket-like enlargement of the external diameter within the terminal area of the discharge and instrument duct, it is possible to convey the duct so far out of the joint that the expanded end catches on the synovium. The position of the hollow cylinder with its sleeve is hereupon fixed from the outside within the area of the skin means of an arresting rider. An application or inserting instrument is employed for introducing the drainage and instrument duct which is removed subsequent to the insertion of the drainage and instrument duct, whereupon a short T-shaped length of tube is mounted on the hollow cylinder. This introduction instrument is connected to securely to the drainage and instrument duct that, during the operation, an automatic loosening of the connection is not possible. The horizontal axis of the cylinder of the T-shaped length of tube is provided with a self-acting inlet and outlet mechanism, while in the vertically branching cylinder or tube of the T-shaped length of tube, a stop cock or stop valve is provided, with the aid of which the drainage into a suction tube can be regulated. After the termination of the operation, the expansion at the end of the hollow cylinder is cancelled and the cylinder together with its sleeve is withdrawn from the joint.

The drainage and instrument duct constructed according to the invention results in the following advantages:

The terminal area of the sleeve expanded in a basket-like manner ensures the position within the joint. Furthermore, the expanded wall section makes it possible for the entire instrument to be made to project into the joint only as little as possible without thereby creating the risk of sliding or slipping out therefrom. Lateral perforations in the hollow cylinder within the area of the basket-lie expanded section of the sleeve 30 afford an additional certainty of a drain that is pen at all times. This system can be fitted directly at the location of the operation without that an accumulation of instruments comes about which would obstruct each each other.

The large internal diameter and the shortness of the hollow cylinder render the effortless introduction of further instruments possible; larger seized meniscus fragments can be removed via this duct without difficulty. It is also possible to make use of instruments that are slightly curved at their points. The suction tube fitted in shunt can be regulated by means of a cock. The recovery of smaller particles for the later histological examination or test is ensured and it is prevented that flushing liquid attempts to escape via other leakage points of the joint and thereby soaks the area surrounding the operation location. The suction tube can be connected to a collecting container in order to render a separation of detached particles from the flushing liquid possible.

Advantageous constructions of the invention are characterized in the subclaims.

Embodiments of the invention are explained in the following with the aid of the drawings. Thus FIG. 1, in a diagrammatical view, shows a drainage and instrument duct comprising a hollow cylinder with a mounted displaceable sleeve, FIG. 2, in a diagrammatical view, shows the drainage and instrument duct in a position rotated through 180° in the longitudinal axis, FIG. 3, in a diagrammatical view, shows the drainage and instrument duct with a wall section expanded at one end, FIG. 4, in a vertical longitudinal section, shows the hollow cylinder with fitted sleeve and a device capably of arresting the sleeve on the hollow cylinder with the aid of an engagement cam engaging into a scale-like section, FIG. 5, in a diagrammatical view, shows a rider for arresting the discharge and instrument duct within an area located outside the skin, FIG. 5, in a front view, shows the arresting rider per FIG. 4, FIG. 7, in a diagrammatical view, shows a T-shaped length of tube with an inlet and outlet mechanism, FIG. 8, in a diagrammatical view, shows the drainage and instrument duct with an inserting instrument connected to the same, the coupling end of which is depicted, FIG. 9, in diagrammatical view, shows the other end of the inserting instrument, FIG. 10, in a diagrammatical view, shows the drainage and instrument duct with attached inserting instrument and mounted suction tube, FIG. 11, in a diagrammatical view, shows the drainage and instrument duct with arrested inserting instrument, FIG. 12, in a diagrammatical view, shows a further embodiment of an inserting instrument that can be connected to the drainage and instrument duct by means of a bayonet catch, FIG. 13, in a diagrammatical view, shows the inserting instrument per FIG. 12 with fitted drainage and instrument duct connected by means of a bayonet catch, FIG. 14, in a diagrammatical view, shows the locking device constructed in the form of a bayonet catch with an additional safety device to safeguard against an inadvertent disengagement of the bayonet catch, FIG. 15, is a diagrammatical view similar to FIG. 14, showing a cam for securing the bayonet catch, FIG. 16, in a vertical longitudinal section, shows the safety device of the bayonet catch, FIG. 17, in a diagrammatical view, shows the drainage and instrument duct with a rider arresting the sleeve in its operative position, FIGS. 18 to 21, in diagrammatical views, show the drainage and instrument duct disposed within the area of a joint for an arthroscopic operation in various positions, and FIGS. 22 to 26, in side views, show the discharge and instrument duct disposed within the area of a joint for an arthroscopic operation in various positions.

Figure 2:
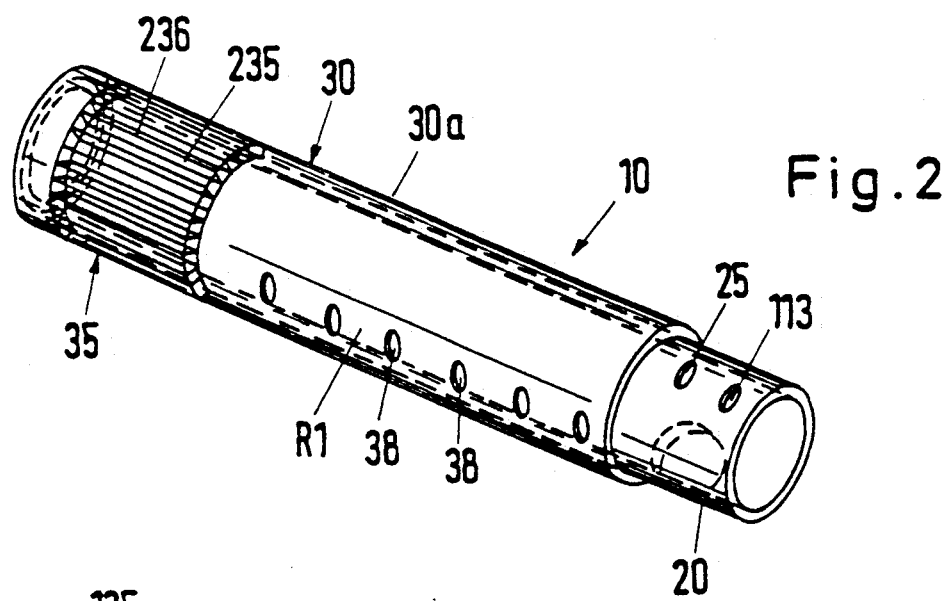
Figure 3:
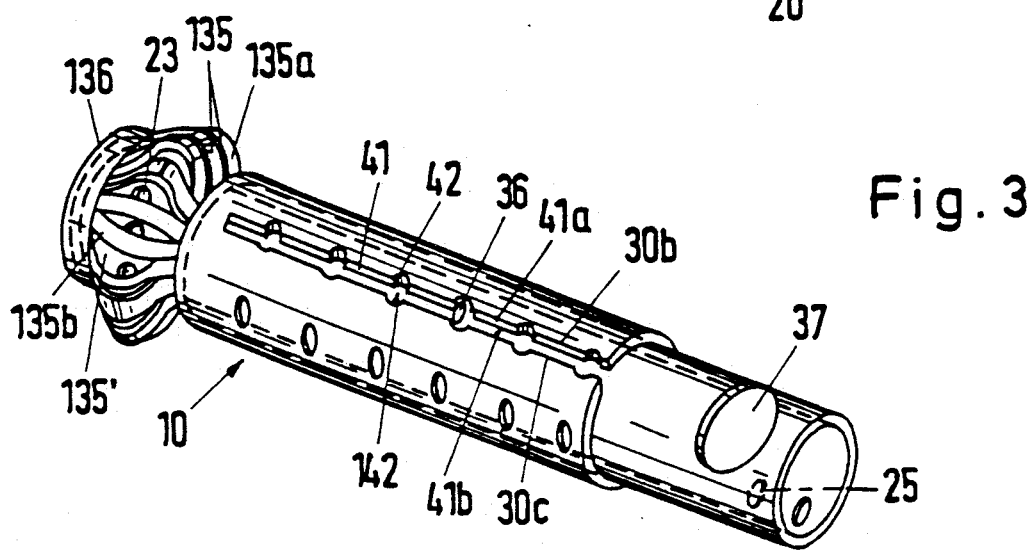

The drainage and instrument duct depicted in the FIGS. 1 to 3 and identified with 10 constitutes a tube-like instrument having a cannula-like character.

This drainage and instrument duct 10 comprises a hollow cylinder 20 and a sleeve 30 that is displaceable on the latter in the longitudinal direction of the hollow cylinder, the length of which, in comparison with the length of the hollow cylinder 20 is dimensioned so as to be shorter. It is intended that the hollow cylinder be dimensioned as short as possible, e.g. approximately 5 cm and to provide with as large as possible an internal diameter, e.g. of approximately 8 mm. The two ends of the hollow cylinder 20 are identified with 21, 22, the hollow cylinder wall with 20a and the sleeve wall with 30a. Within the area of their ends 21, 31, the hollow cylinder 20 and the sleeve 30 are interconnected so as to be flush with each other and, within these terminal areas, are constructed so as to be closed.

Figure 17:
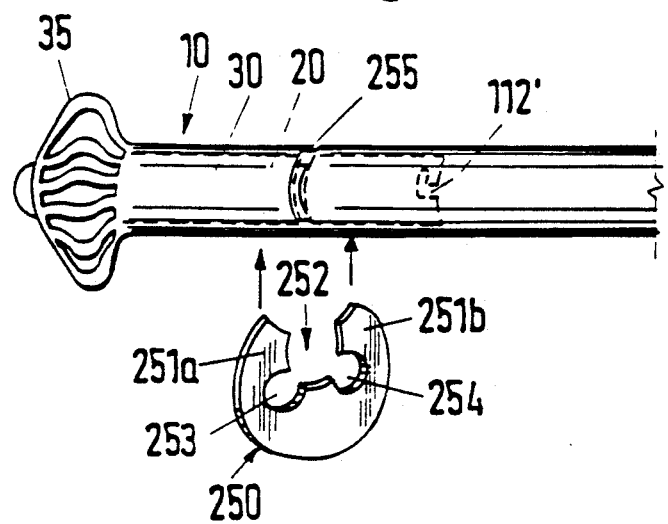

The wall section 35 of the sleeve located within the area of the end 31 of the sleeve 30 is constructed in such a way that said wall section 35, when the sleeve 30 is displaced in the direction of the arrow X, expands outwardly in a basket-like manner while forming a number of slot-shaped perforations 135' arranged across the circumference and extending parallelly to each other so that a drainage and instrument duct 10 is obtained which, within its terminal area, possesses a wall section 35 which enlarges the external diameter of the sleeve (FIG. 17).

Within the area of the expandable wall section 35, the hollow cylinder is provided with a number of perforations 23 disposed so as to be distributed over the hollow cylinder circumference. The wall section expansion of the sleeve 30 is maintained by an arresting—still to be described in greater detail in the following —of the sleeve 30 displaced on the hollow cylinder 20 (FIG. 3). For this purpose, the sleeve 30 is provided with a means 40 that interacts with the hollow cylinder 20 which arrests the sleeve on the wall 20a of the hollow cylinder 20, which will be described in greater detail in the following. The hollow cylinder 20, on its end 22, is provided with a guide cam 25 for the sleeve 30 (FIG. 2) secured to the hollow cylinder wall 20a.

The wall section 35 of the sleeve 30 that is outwardly expandable in a basket-like manner comprises a number of lamellar or web-like shaped members 135 disposed so as to be distributed over the sleeve circumference and extending in the longitudinal direction of the sleeve, which, with their ends, 135a, are secured to the body of the sleeve 30 and, with their other ends 135b, to an annular member 136 which is rigidly connected to the hollow cylinder 20. The annular member 136 forms, with the body of the sleeve 30 over the lamellar shaped members 135, one structural unit (FIG. 3).

However, the expandable wall section 35 of the sleeve 30 may also be formed of a number of slots 236 constructed in the wall 30a of the sleeve 30 disposed so as to be distributed over the circumference and extending in the longitudinal direction of the sleeve and the strip-like wall sections 235 remaining, in each case, between the slots 236, in which case said wall sections 235 correspond to the lamellar shaped members 135 (FIG. 2). The lamellar shaped members 135 and the strip-like wall sections 235 of the sleeve 30 are of thin-walled construction; they consist of a springily resilient material so that, when the sleeve 30 is displaced in the direction of arrow X, said lamellar shaped members 135 or the strip-like wall sections 235, respectively, are expanded in the outward direction (FIGS. 1 and 3).

The sleeve 30 can be locked on the hollow cylinder 20 with an outwardly expanded wall section 35 with the aid of the means 40. Said means 40 for locking the sleeve 30 on the hollow cylinder 20 comprises a slot 41 extending on the longitudinal direction of the sleeve and terminating in the end 32 which faces away from the expandable wall section 35 of the sleeve 30 and constructed in the wall of the hollow cylinder. In the oppositely located longitudinal rims 41a, 41b of the wall sections 30b, 30c of the sleeve 30 delimiting the slot 41, pitch-circular recesses 42, 142 are constructed at regular or irregular intervals, the recesses 42 in the wall section 30b are located so as to be opposite the recesses 142 in the wall section 30c so that two oppositely located recesses 42, 142 each complement one another so as to form an approximately circular recess 45. In order to be able to arrest the sleeve 30 on the hollow cylinder 20, the hollow cylinder 20 is provided with a locking cam 36 located within the area of the slot 41 of the sleeve 40, whose shape and diameter correspond approximately to the circular recesses 45 which are formed by the oppositely located recesses 42, 142. The width of the slot 41 in the sleeve 30 is dimensioned in such a way that, when the hollow cylinder 20 is inserted into the interior of the sleeve 30, the locking cam 36 can be introduced into the slot 41 while the wall sections 30a, 30b of the sleeve 30 delimiting the slot 41 and located opposite each other are simultaneously slightly expanded so that, when a recess 45 is reached, the locking cam 36 is retained in said recess 45 and the sleeve 30 is immocably secured thereby on the hollow cylinder 20 (FIG. 3). The slot 41 in the wall 30a of the sleeve 30 is constructed so as to extend in the longitudinal direction of the sleeve and terminates in the sleeve aperture within the area of the end 32 of the sleeve 30.

Instead of a locking means 40 constructed in this way, it is also possible to effect the locking of the sleeve 30 on the hollow cylinder 20 by means of suitable, differently constructed devices, e.g. with the aid of engagement means and the like. Due to the number of the recesses 45 constructed within the area of the slot 41 of the sleeve 30 and due to the oppositely located recesses 42, 142, the sleeve 30 can be arrested on the hollow cylinder 20 in every position so that it is possible to vary the size of the circumference of the basket-lie terminal expansion of the sleeve 30 in accordance with the respective requirements. The locking cam 36 may also be constructed so as to be pressed inwardly so as to render possible a displacement of the sleeve 30 in the direction of arrow X1 while the locking cam 36 assumes the inwardly pressed position. In this embodiment, the locking cam 36 is constructed so as to be automatically resettable, which may be effected by means of an appropriate material selection.

A further embodiment of a locking device 40 for the sleeve 30 on the hollow cylinder 20 is depicted in the FIG. 4. According to this the means 40 consists of a scale-like sectional body 280 disposed on the inner wall of the sleeve 30 and of an engagement cam 281 on the outer wall of the hollow cylinder 20, in which the scale selection 282 of the sectional member 280 is provided with detent edges 283 for the enegagement cams 281 which face the rearward end of the sleeve 30. For disengaging the detent, the engagement cam 281 can be constructed so as to be swivelled or withdrawn into the wall of the hollow cylinder 20.

The locking of the sleeve 30 on the hollow cylinder 20 and the insertion of the drainage and instrument duct 10 into the area of a joint for an arthroscopic operation according to FIGS. 18 to 21 and FIGS. 22 to 26 is effected with the aid of an application or inserting instrument 110 which, when being fitted on to the hollow cylinder 20, brings about an advance of the sleeve 30 in order to expand the terminal wall section of the drainage and instrument duct 10 in a basket-like manner or to dilate the same and to maintain it in the expanded position, which, according to FIG. 17, is effected with the aid of a rider 250 mounted on the hollow cylinder 20, to which reference will be made in greater detail in the following.

Within the area of its end 22, the hollow cylinder 20 possesses a further Largish aperture 37 (FIG. 1).

The hollow cylinder 20 and the sleeve 30 consist of suitable materials, particularly steel or other materials suited for the manufacture of sets of surgical instruments. However, it is also possible for other suitable materials to be employed.

Figure 21:
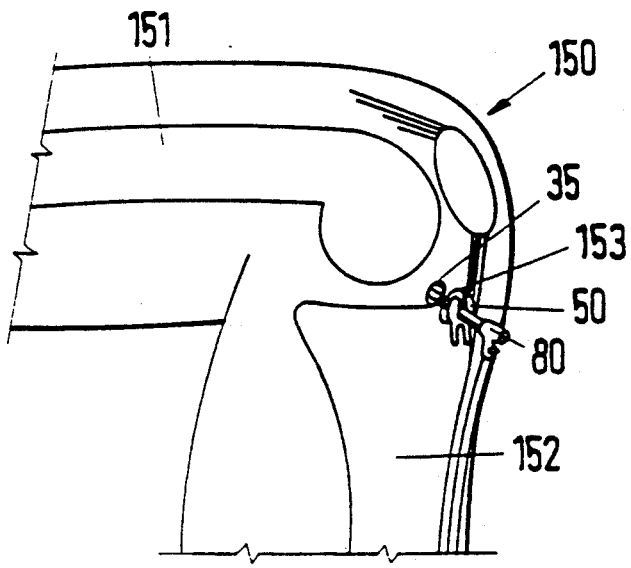

In order to be able to secure the drainage and instrument duct 10 in the operative position in its, in each case, requisite position, a lockable rider 50 is provided on the drainage and instrument duct 10. Said rider is lockably retained on the sleeve embracing the hollow cylinder 20 and embraces the wall 30a of the sleeve 30 (FIG. 21).

According to the FIGS. 5 and 6, this rider consists of an H-shaped formed member 51, whose lateral longitudinal legs are identified with 52,53 and the web centrally interconnecting the longitudinal legs with 54. The leg sections 52a,53a located above the web interconnecting the two longitudinal legs 52,53 are constructed in the form of a pitch circle and complement each other so as to form an open ring 55 while the two free ends 52a',53a' of the leg sections 52a,53a are arranged so as to be located opposite each other (FIG. 6). The interspace between these two ends 52a',53a' of the two leg sections 52a,53a is indicated with 56. The distance separating the two ends 52a',53a' of the leg sections 52a,53a is dimensioned in such a way that, when the leg sections 52a,53a are simultaneously slightly spread apart in the direction of arrow X1, the rider 50 can be mounted on the sleeve 30 so that both leg sections 52a53a embrace the outer wall area of the sleeve 30 in sections. The circular area 55a delimited and enclosed by the two leg sections 52a,53a possesses a diameter corresponding approximately to the external diameter of the sleeve 30.

The slight lateral spreading apart of the leg sections 52a,53a of the rider 50 in the direction of arrow X1 is achieved with the aid of the lower leg sections 52b,53b of the longitudinal legs 52,53 of the rider 50 which are constructed in the manner of a handle (FIG. 5). The web 54 which interconnects the two longitudinal legs 52,53 of the rider 50 is dimensioned so as to be short in length and is constructed with thin walls and consists preferably of springily resilient materials so that, when the lower legsections 52b,53b are compressed in the direction of arrow X2, the two upper leg sections 52a,53a are spread apart in the direction of arrow X1. Instead of springily resilient construction of the web 54 of the rider 50, this elasticity and a simultaneous elastic recovery capacity connected therewith can also be achieved by the selection of a suitable material. Thus the possibility exists, for example, of fabricating the rider 50 of plastic or of steel, in which case the web 54 is then kept in its dimensions in such a way that a bending aside of the web 54 within the area identified with 54a is possible (FIG. 6).

For positionally securing the rider on the sleeve 30, said rider 50 possesses, on the internal edges 57,57' facing each other of the two upper leg sections 52a,53a, two oppositely located engagement cams 58,59 and a further engagement cam 60 which is mounted between the engagement cams 58,59 on the internal edges 57" located within the area of the web 54 of the shaped member 51 so that the two engagement cams 58,59 come to be located opposite each other and the cam 60 centrally and below these two engagement cams 58,59 (FIG. 6).

For locking the rider 50 on the sleeve 30, the sleeve, which is seated on the hollow cylinder 20, is provided in its wall 30a with three rows R,R1,R2 of consecutively disposed perforations 38 extending in the longitudinal direction of the sleeve, the two rows R,R1, being located opposite each other, whereas the row R2 is located centrally and below the two rows R,R1 (FIGS. 1 and 2). Each row R,R1,R2 possesses a number of perforations 38 located at a distance from each other, it being possible to have regular or also irregular intervals between the perforations 38. The arrangement of these three rows R,R1,R2 with the perforations 38 is in conformity with the disposition of the engagement cams 58,59,60 of the rider 50 so that, when the rider is placed upon the sleeve 30, the three engagement cams 58,59,60 engage in each case into three recesses 45 located within a plane extending vertically relative to the longitudinal axis of the sleeve. In the FIGS. 1 to 3, the rows R and R1 are depicted so as to be visible with their perforations 38, whereas the row R2 is not visible.

The two upper leg sections 52a,53a of the shaped member 51 of the rider 50 are preferably configured so as to correspond to the circumference of the sleeve 30, especially since both the hollow cylinder 20 as well as the sleeve 30 may possess other cross-sectional surface forms that circular ones.

The end of the hollow cylinder 20 which faces away from the expandable wall section 35 of the sleeve 30 is constructed in the form of a connecting branch 70 for a T-shaped piece of tube 80 (FIGS. 1 and 7). The horizontally extending cylinder 81 of the T-shaped length of tube is provided with an automatically closing inlet and outlet means 90 which comprises a centrally perforated rubber diaphragm, the central perforation of which can be additionally closed by a rubber lip located inside. The vertically extending cylinder or socket 82 of the T-shaped length of tube 80 is provided with a stop valve, a stop cock or the like 83. The free end 82a of the cylinder 82 is constructed in in the form of a connecting branch 84 for a suction hose not indicated in the drawing. The inlet and outlet means 90 may be disposed and constructed in the interior of the horizontally extending cylinder 81 of the T-shaped length of tube 80, the possibility also exists of constructing the inlet and outlet means 90 in the form of a cover or closure cap 91, in which case the closure cap 91 is retained with the aid of a band, elastic web or the like 92 on the outer wall of the T-shaped length of tube 80 and can be placed upon the free open end 81a of the horizontal cylinder 81 of the T-shaped length of tube 80 (FIG. 7). The T-shaped length of tube 80 can be attached by means of a plug connection, clamping connection of bayonet catch 100 on the outer wall of the hollow cylinder 20. The attachment is effected while making use of the guide cam 25 on the wall 20a of the hollow cylinder 20. The free end 81b of the horizontal cylinder 81 of the T-shaped length of tube 80 is provided with an engagement perforation 101 so that the T-shaped length of tube 80 can be secured on the hollow cylinder 20 after the manner of a bayonet catch. The cover 90 of the T-shaped length of tube 80 is mounted on the free end 81a of the horizontal cylinder 81 when the T-shaped length of tube 80 is used and is dismounted only when a large fragment has to be removed.

As is shown in FIGS. 8 to 11, the drainage and instrument duct 10 can be connected to an inserting instrument 110, the method of operation of the applicator consists in securely retaining a suction tube 118, to advance the suction tube 118 far into the joint, to trigger the spreading of the outwardly expandable wall section 35 and to withdraw the hollow cylinder 20 as far as the limit stop, in the process a removal of the application instrument has to be possible as well.

This application instrument 110 comprises a socket 11 that is insertable into the interior of the hollow cylinder 20 (FIG. 8). Said socket 111, on its end 111a facing the hollow cylinder 20, carries a locking means, such as locking cams 112 or a bayonet catch 112', the locking cam 112 can be engaged into a perforation 113 constructed in the wall 20a of the hollow cylinder 20 within its terminal area 22 (FIGS. 2, 10 and 11). In addition, the inserting instrument 110 comprises a sleeve tube 114 embracing the socket 111, the external diameter of which corresponds approximately to the external diameter of the hollow cylinder 20. Said sleeve tube 114, which can be displaceable in the longitudinal direction of the tube, in its wall 114a, is provided with a guide groove 115 extending approximately transversely to the longitudinal direction of the tube, as can be seen from FIGS. 8 and 10. This guide groove 115 interacts with the guide cam 25 formed on to the outer wall area of the wall 20a of the hollow cylinder 20 within its terminal area 22 (FIG. 2). By rotating the sleeve tube 114 about its longitudinal axis in the direction of arrow Y, said guide cam 25 of the hollow cylinder 20 is introduced into the guide groove 115 and, by virtue of the guidance of the guide groove 115 which appears from FIG. 8, the sleeve tube 114 is pressed against the sleeve 30 of the hollow cylinder 20 in such a way that the wall section 35 of the sleeve 30 is expanded (FIGS 3 and 10).

Furthermore, the inserting instrument 110 comprises an adapting piece 116 with a suction hose connection branch 117 (FIG. 8). Said adapting piece 116 carries centrally a suction tube 118 passed through the interior of the first socket 111, which terminates in the suction hose connection branch 115 of the adapting piece. When coupling the application instrument 110 to the drainage and instrument duct 10, the free end of the suction tube 118a is located within the area of the hollow cylinder 20.

On their free ends 111b, 114b, the two tubes 111,114 carry annular or disk-shaped handles 119,120 in order to ensure an effortless handling of both sockets 111,114.

The adapting piece 116 can be coupled to the handle 119. For this purpose, the disk-shaped section 116a of the adapting piece 116 is provided with a cam 116b facing the disk-shaped handle 119 which engages into a corresponding recess 119b in the handle As is revealed by FIGS. 8 and 10, the drainage and instrument duct 10 is disposed so as to be eccentric to the longitudinal axis of the inserting instrument 1110. If the suction tube 118 is rotated by means of the adapting piece 116, then flushness between the drainage and instrument duct 10 and the inserting instrument 110 or its socket is achieved which simultaneously engages into the cam 112 (FIG. 11). In addition, the cam 25 engages into the guideway 115 of the sleeve tube 114 so that a secure locking is achieved. If the adapting piece 116 is placed upon the disk-like handle 119 and locked with the same, then a secure connection between the drainage and instrument duct 10 is ensured. During the advance due to the rotation of the sleeve tube 114 by means of the engagement of the cam 25 into the guideway 115, an advance of the sleeve 30 on the hollow cylinder 20 takes place simultaneously with the result that the terminal section of the sleeve is expanded in a basket-like manner.

According to FIGS. 12 to 16, the locking of the drainage and instrument duct 10 with the inserting instrument 110 is effected by means of a bayonet catch 112'. The inserting instrument 110' to be connected with the drainage and instrument duct 10 consists of a socket 111' that is to be inserted with its end 111a' into the interior of the hollow cylinder 20 which, on its end 111a' facing the hollow cylinder 20, is provided with a bayonet catch 112' as a locking means, which comprises an L-shaped recess 113' in the wall of the hollow cylinder 20 and a cam 113a' engaging into the recess 113', and longitudinally displaceable sleeve tube 114 disposed on the socket 111', which is connected to a suction tube connection branch 117 (FIGS. 12 and 13).

The inserting instrument 110' is, with its front socket, slipped on to the hollow cylinder 20 so that the socket 111' overlaps the hollow cylinder 20. Within the area of the overlap area, the hollow cylinder 20 carries the cam 113a' which, when the socket 111' is slipped on to the hollow cylinder, is pressed in and, by means of a compression spring or the like, springs back into its locking position so that then, when the socket 111' is rotated, the cam 113a' engages into the section of the recess 113' extending transversely to the longitudinal direction of the socket 111' (FIGS. 13, 14 and 15).

Figure 16:
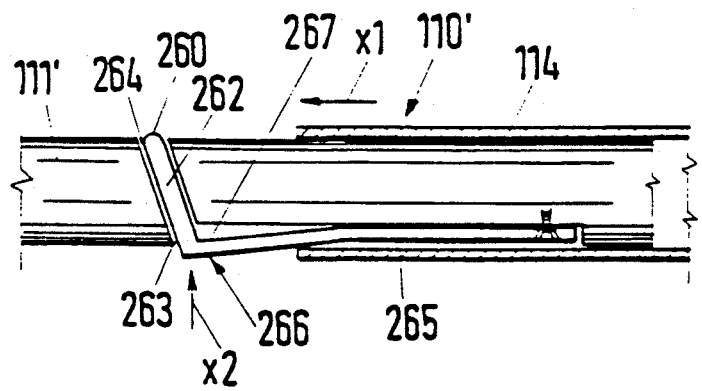

For securing the bayonet catch 112', the socket 111' is provided with a cam 260 which is insertable into the recess 113' by advancing the sleeve tube 114 which, when the sleeve tube 114 is returned is transferred from the locking position into a release position. Said locking cam 260 is formed by an L-shaped locking rod 261, one of whose legs 262 has a length which is greater than the diameter of the socket 111' and which is passed through perforations 263, 264 which are disposed slightly staggered or fully coincident with each other in the wall of the socket 111', while the other longer leg 265 of the locking rod 261 is retained, at its end, in a recess 267 while forming an outwardly angled area 266. The sleeve tube 114 overlaps the socket 111' within the area of the attachment of the locking rod 261 while the outwardly angled section 266 of the leg 265 of the locking rod 261 is located at right angles to the shorter leg 262. If the sleeve tube 114 is advanced in the direction of arrow X1, then the sleeve tube overtravels the angled section 266 of the locking rod 261 with the result that the leg 262 with its end 260 forming the cam is raised in the direction of the arrow X2 and is inserted into the recess 113' of the bayonet catch 112' (FIG. 16). A rotational safeguard for the discharge and instrument duct is achieved by this.

In order to arrest the sleeve 30 on the hollow cylinder 20 in the sleeve position in which the sleeve end is expanded in a basket like manner (FIG. 17), the hollow cylinder 20 is provided with an annular groove 255 in its outer wall area for accommodating the legs 251a, 251b of a locking or arresting rider 250 mounted on the hollow cylinder 20 which is clampingly retained on hollow cylinder.

According to FIG. 17, the rider 250 comprises an approximately U-shaped formed member 251 with springily resilient legs 251a,251b which embrace the hollow cylinder 20 which, on the inner wall side, possess a profile which corresponds to the profile of the hollow cylinder. The The shaped member 251 is provided with two apertures 253,252 that are connected with the hollow cylinder accommodating aperture 252 of the rider 250 for receiving hoses, cables or the like. The rider 250 is clampingly retained on the hollow cylinder 20 in order to prevent a sliding back of the sleeve 30 out of the operative position with basket-like expanded terminal circumference of the sleeve 30 into the starting position.

The annular groove 255 on the hollow cylinder 20 is disposed in such a way that subsequent to a forward sliding of the sleeve 30 with the aid of the sleeve tube 114 and subsequent to the effected spreading or expansion of the sleeve end, the sleeve 30 is arrested on the hollow cylinder 20. By detaching the rider 250 from the hollow cylinder 20, the sleeve 30 is released and is moved back into its starting position (FIGS. 1 and 2). By this return movement of the sleeve 30, the expansion at the end of the sleeve is cancelled. The return movement of the sleeve 30 on the hollow cylinder 20 can in this case be brought about by a compression or tension spring or by some other elastic member.

The handling of the drainage and instrument duct 10 is described in the following in greater detail with the aid of the FIGS. 18 to 26.

Figure 18:
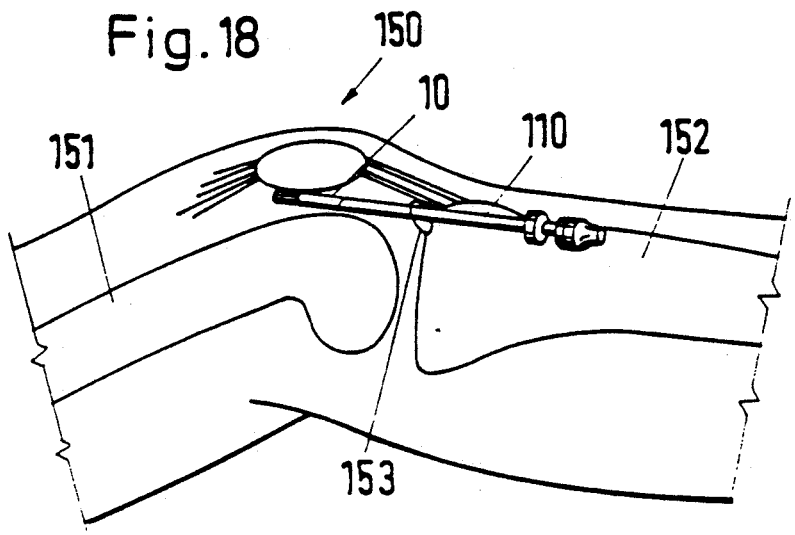
Figure 19:
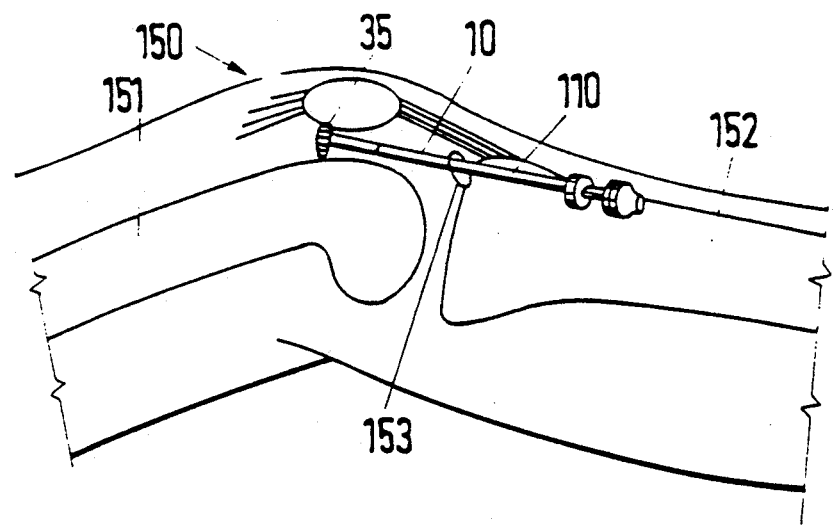
Figure 20:
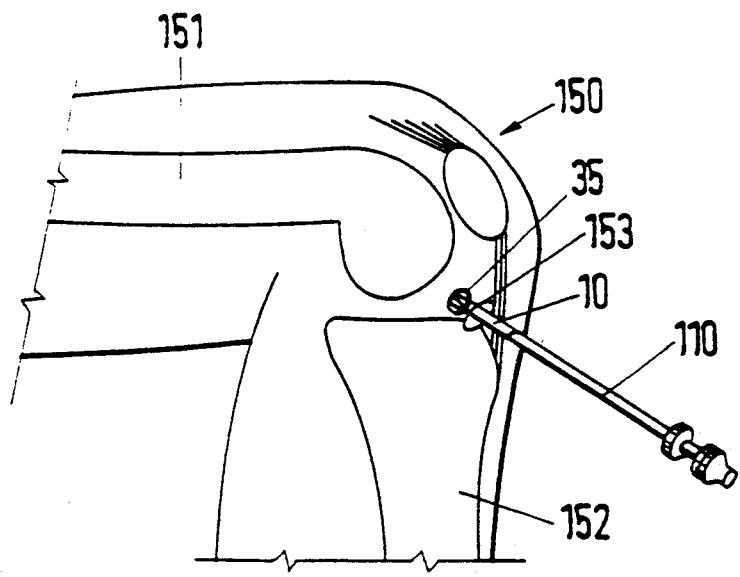

A joint is identified with 150 and the two bones forming the joint with 151,152. With 153, the aperture effected in the skin surroundings the joint for inserting the drainage and instrument duct 10. The drainage and instrument duct 10 is inserted as far as into the joint area through this aperture 153 in the skin and this is done by employing the guiding or application or inserting instrument 110 which serves at the same time to guide the duct 10 (FIG. 18). Due to the hollow cylinder 20 being dimensioned so as to be short, the possibility exists of advancing the hollow cylinder with its sleeve 30 far into the joint so that a secure position in the joint is ensured. By an appropriate actuation of the application instrument 110, on the free end of the hollow cylinder 20, by a displacement of the sleeve 30, the wall section 35 is expanded and a significant increase in the external diameter is obtained (FIGS. 19, 24 to 26). Following this, the hollow cylinder 20 is moved out of the joint with the outwardly expanded wall section 35 so far until the expanded section catches on the synovium (FIG. 20). This position of the hollow cylinder 20 is now fixed from the outside at the level of the skin with the rider 50. The guiding or application instrument 110 is thereupon removed and the T-shaped length of tube 80 having small dimensions is then fitted on to the hollow cylinder 20 (FIG. 21). Said T-shaped length of tube, in the axis of the horizontal cylinder 81, supports the self-acting inlet and outlet mechanism 90. In the vertically branching tube or cylinder 82 of the T-shaped length of tube 80, the drainage into a suction hose not depicted in the drawing can be regulated by means of a stop cock or stop valve 83. After the termination of the operation, the expansion is cancelled and the hollow cylinder 20 is withdrawn from the joint.

In the handling of the drainage and instrument duct 10 shown in FIGS. 22 to 26, no rider 250 is provided. The drainage and instrument duct can also be employed without a rider 250; in this case the arresting of the sleeve 30 on the hollow cylinder 20 is effected with expanded sleeve end with other technical means described in the foregoing. For the return movement of the drainage and instrument duct 10, the sleeve locking is released and, by the return movement of the sleeve tube 114, the sleeve end is brought back from the expanded position (FIG. 3) into the initial position (FIG. 1).

In the operative position, the expanded end of the sleeve 30 possesses approximately the form of a sphere or of an ellipsoid (FIG. 3).

I claim:

1. Drainage and instrument duct for the arthroscopy, characterized in that the drainage and instrument duct (10) is formed by a hollow cylinder (20) and a sleeve (30) disposed on the hollow cylinder (20) and displaceable in the longitudinal direction of the hollow cylinder, the length of which, in comparison with the length of the hollow cylinder (20), is dimensioned so as to be shorter, the hollow cylinder and the sleeve being interconnected at their ends (21,31) so as to be flush and in that the sleeve (30) is provided with a wall section (35) which, when the sleeve (30) is longitudinally displaced towards the end (21) of the hollow cylinder (20), is outwardly expandable and, after the fashion of a basket, enlarges the external diameter of the sleeve and is provided with a number of perforations (135) which are so disposed as to be distributed over the circumference and in side-by-side arrangement, wherein the drainage and instrument duct (10) is connected to an application or inserting instrument (110) which comprises a socket (111) that can be inserted with its end (111a) into the interior of the hollow cylinder (20), which, at its end (111a) facing the hollow cylinder (20), carries a locking means, such as a locking cam (112) or a bayonet catch (112') which is engageable into a perforation (113,113') constructed in the wall (20a) of the hollow cylinder (20) on the terminal area (22) of the same, a longitudinally displaceable sleeve tube (114) which embraces the socket (111), the external diameter of which corresponds approximately to the outer diameter of the hollow cylinder (20) and which, in its wall (114a), is provided with a guide groove (115) extending approximately transversely to the longitudinal direction of the socket, said guide groove interacts with a guide cam (25) formed on to the outer wall (20a) of the hollow cylinder (20) within its terminal area, and a disk-shaped adapting piece (116) with a suction hose connecting branch (117) which centrally supports a suction tube (118) passed through the interior of the first socket (111), in which the socket (111) and the sleeve tube (114), on their respective free ends (11b,114b), carry annular or disk-shaped handles (119,120), of which the handles (119,120) and the handle (119) can be detachably interlocked with the adapting piece (116), while, by rotating and advancing the sleeve tube (114), the basket (35) is expanded and the sleeve (30) is arrested in the advanced position.

2. Drainage and instrument duct according to claim 1 characterized in that the hollow cylinder (20), on its end (2) that faces away from the expandable wall section (35) of the sleeve (30) is provided with a perforation (38).

3. Drainage and instrument duct according to claim 1 characterized in that the end (32) of the hollow cylinder which faces away from the expandable wall section (35) of the sleeve (30) is constructed in the form of a connecting branch (70) for a T-shaped length of tube (80), whose horizontally extending cylinder (81) is provided with an automatically closing inlet and outlet means (90) which consists of a centrally perforated rubber diaphragm, in which the vertically extending cylinder (82) of the T-shaped length of tube (80) is provided with a stop valve (83) and, at the free end (82a), is constructed in the form of connecting branch (84) for a suction hose.

4. Drainage and instrument duct according to claim 3, characterized in that the central perforation of the rubber diaphragm is sealed by an internally located rubber lip.

5. Drainage and instrument duct according to claims 3 and 19, characterized in that the inlet and outlet means (90) is constructed in the form of a cover or closure cap (91) which, by means of a band, elastic web or the like (92) is retained on the outer wall of the T-shaped length or tube (80) and which can be mounted on the free open end (81a) of the horizontal cylinder (81) of the T-shaped length of tube (80).

6. Drainage and instrument duct according to claim 3, characterized in that the T-shaped length of tube (80) can be secured to the wall of the hollow cylinder (20) with the aid of a plug connection, clamping connection or bayonet catch.

7. Drainage and instrument duct according to claim 1, characterized in that the drainage and instrument duct (10) can be connected to an application or inserting instrument (110') which comprises a socket (111') that can be inserted with its end (111a') into the interior of the hollow cylinder (20) and which, on tis end (111a') facing the hollow cylinder (20), carries a locking means such as a bayonet catch (112') consisting of an L-shaped recess (113') in the wall of the hollow cylinder (20) and a cam (113a') engaging into the recess (113') and a longitudinally displaceable sleeve tube (114) disposed on the socket (111') that is connected to a suction tube connecting piece (117).

8. Drainage and instrument duct according to claim 7, characterized in that, in order to secure the bayonet catch (112') the socket (111') is provided with a cam (260) that is insertable into the recess (113') by advancing the sleeve tube (114), which, when the sleeve tue (114) is returned from the locking position, is transferred into a release position.

9. Drainage and instrument duct according to claims 7 and 8, characterized in that the locking cam (260) is formed by an L-shaped locking rod (261), one of the legs (262) of which possesses a length which is greater than the diameter of the socket (111') and which is passed through perforations (263,264) in the wall of the socket (111') which are disposed so as t be slightly staggered or coincident with each other, while the other, longer led (265) of the locking rod (261), while forming an outwardly angled area (266), is retained at the end in a recess (267) constructed in the outer wall area of the socket (111'), in that the sleeve tube (114) overlaps the socket (111') within the area where the locking rod (261) is secured, and in that the outwardly angled section (266) of the leg (265) of the locking rod (261) is at right angles to the shorter leg (262).

* * * * *